United States Patent
Bates

(10) Patent No.: US 10,052,636 B2
(45) Date of Patent: *Aug. 21, 2018

(54) METHOD AND SYSTEM FOR PROCESSING WHOLE HEMP STALKS

(71) Applicant: Hemp Sense Inc., Gilbert Plains (CA)

(72) Inventor: Lyall D. Bates, Gilbert Plains (CA)

(73) Assignee: Hemp Sense Inc., Gilbert Plains (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/821,093

(22) Filed: Nov. 22, 2017

(65) Prior Publication Data

US 2018/0093275 A1    Apr. 5, 2018

Related U.S. Application Data

(63) Continuation of application No. 15/147,003, filed on May 5, 2016, now Pat. No. 9,855,562.

(30) Foreign Application Priority Data

May 7, 2015    (CA) ........................ 2890428
Dec. 9, 2015    (CA) ........................ 2914313

(51) Int. Cl.
| | | |
|---|---|---|
| *B02C 23/10* | (2006.01) | |
| *B02C 23/20* | (2006.01) | |
| *D01B 9/00* | (2006.01) | |
| *A01K 1/015* | (2006.01) | |
| *A61K 36/185* | (2006.01) | |
| *B01J 2/00* | (2006.01) | |
| *C11B 1/10* | (2006.01) | |

(52) U.S. Cl.
CPC ............ *B02C 23/10* (2013.01); *A61K 36/185* (2013.01); *B02C 23/20* (2013.01); *D01B 9/00* (2013.01); *A61K 2236/15* (2013.01); *A61K 2236/30* (2013.01); *B01J 2/00* (2013.01); *C11B 1/10* (2013.01); *C11B 1/104* (2013.01)

(58) Field of Classification Search
None
See application file for complete search history.

(56) References Cited

U.S. PATENT DOCUMENTS

| | | | | |
|---|---|---|---|---|
| 8,034,449 B1 * | 10/2011 | Dooley | .................. | B27L 11/02 |
| | | | | 144/373 |
| 9,707,567 B2 * | 7/2017 | Bates | ....................... | D01B 9/00 |
| 9,855,562 B2 * | 1/2018 | Bates | ..................... | B02C 23/10 |

(Continued)

FOREIGN PATENT DOCUMENTS

| | | | |
|---|---|---|---|
| CA | 2328853 | * | 11/1999 |
| CA | 2824596 | * | 7/2012 |
| CN | 1651647 | * | 8/2005 |

*Primary Examiner* — Mary Lynn F Theisen
(74) *Attorney, Agent, or Firm* — Kyle R. Satterthwaite; Abe + Company Inc.; Ryan W. Dupuis

(57) ABSTRACT

A method and system for processing whole hemp stalks is disclosed. The method and system use an entirety of the whole hemp stalks in producing the particulate hemp such that the particulate hemp comprises both bast fiber and shire of the original whole hemp stalks. Additionally, hemp crumbs or crumbles may be processed from whole hemp stalks, or from particulate hemp which is larger than the hemp crumbs such as hemp pellets. The hemp crumbs may be formed by crushing the hemp pellets.

23 Claims, 2 Drawing Sheets

(56) References Cited

U.S. PATENT DOCUMENTS

2011/0232173 A1\* 9/2011 Lefebvre ............ A01G 13/0262
  47/9
2014/0183791 A1\* 7/2014 Duncan ..................... C10L 5/32
  264/330

\* cited by examiner

METHOD AND SYSTEM FOR PROCESSING WHOLE HEMP STALKS

This application is a continuation of U.S. patent application Ser. No. 15/147,003 filed May 5, 2016, which claims the benefit of Canadian Patent Application Serial No. 2,890,428 filed May 7, 2015 and Canadian Patent Application Serial No. 2,914,313 filed Dec. 9, 2015 each of which is incorporated by reference herein.

FIELD OF THE INVENTION

The present invention relates to processing hemp bast fiber and hemp shive or hurds, and more particularly to an economical and efficient manner of processing hemp.

BACKGROUND

Use of hemp in consumer products and the like has increased in recent years. Hemp is grown in Canada, where hemp stalks covered 75,000 acres of agricultural land in 2014.

SUMMARY OF THE INVENTION

According to an aspect of the invention there is provided a method of processing whole hemp stalks at a single location, each whole hemp stalk including bast fiber and shive, the method comprising:
  providing the whole hemp stalks at said location;
  at said location, reducing the whole hemp stalks into particulate hemp which is smaller in size than the whole hemp stalks and still includes bast fiber and shive;
  at said location, processing the particulate hemp without separating bast fiber and shive including:
    reducing the particulate hemp in size so as to lie in a first size range so as to be usable for further processing of the particulate hemp into one of a plurality of different products each with different size;
  wherein the particulate hemp includes unseparated bast fiber and shive throughout the step of processing the particulate hemp.

According to another aspect of the invention there is provided a system of processing whole hemp stalks into particulate hemp at a single location, wherein the whole hemp stalks have been harvested and each of the whole hemp stalks includes bast fiber and shive, the system comprising:
  a preliminary size reduction station arranged at said location for reducing the previously harvested whole hemp stalks into particulate hemp, which is smaller in size than the whole hemp stalks and still includes bast fiber and shive;
  a processing stage arranged at said location for processing the particulate hemp without separating bast fiber and shive, the processing stage including:
    a first size reduction station arranged for reducing the particulate hemp in size so as to lie in a first size range so as to be usable for further processing of the particulate hemp into one of a plurality of different products each with different size;
    at least one further size alteration station receiving the particulate hemp sized in the first size range as input thereto for said further processing so as to derive a selected one of said plurality of different products;
  wherein the particulate hemp includes unseparated bast fiber and shive throughout the processing stage.

According to another aspect of the invention there is provided a method of processing whole hemp stalks, each whole hemp stalk including bast fiber and shive, the method comprising:
  providing the whole hemp stalks;
  reducing the whole hemp stalks into particulate hemp, which is smaller in size than the whole hemp stalks and still includes bast fiber and shive;
  processing the particulate hemp, which includes:
    reducing the particulate hemp in size so as to lie in a first range between 25 microns and 500 microns;
  wherein the particulate hemp includes bast fiber and shive throughout the step of processing the particulate hemp.

In the embodiment as described in more detail hereinafter, the particulate hemp is sized into one of several forms including hemp fines or flour, hemp pellets, and hemp crumbs (which are also termed hemp crumbles). Each hemp product, which is differentiated from one product to another by particle size, is advantageous for certain applications based on physical form, as will become apparent later. The present embodiment is suited for using an entirety of the hemp stalks for producing the particulate hemp therefrom. As such, processing the hemp stalks to form the particulate hemp may be less expensive than prior art processes in which the constituent components of the hemp stalks such as the bast fiber and the shive are separated from one another before processing into the particulate hemp.

As the particulate hemp includes bast fiber and shive, close to 100% of the whole hemp stalks, if not all thereof, is processed into the particulate hemp. As such, separation of bast fiber and shive is not required.

'Pulverize' as used in this specification means 'to reduce to fine particles.'

'Hemp crumbs' may also be called 'hemp crumbles'; irrespective of the particular term used, 'crumb' or 'crumble' as used in this specification refer to a small particle or portion of something—in this case of hemp.

The step of reducing the particulate hemp in size so as to lie in the first range between 25 microns and 500 microns may be performed using a hammer mill.

In one instance, the particulate hemp comprises an average dimension between 1.10 centimeters and 7.70 centimeters after the step of reducing the whole hemp stalks into particulate hemp but prior to the step of processing the particulate hemp. In another instance, the particulate hemp comprises an average dimension between 1.30 centimeters and 6.40 centimeters after the step of reducing the whole hemp stalks into particulate hemp but prior to the step of processing the particulate hemp. In a further instance, the particulate hemp comprises an average dimension between 1.50 centimeters and 5.30 centimeters after the step of reducing the whole hemp stalks into particulate hemp but prior to the step of processing the particulate hemp.

The step of reducing the whole hemp stalks into particulate hemp may be performed using a shredder.

"Average dimension" refers generally to an average of respective maximum dimensions of a unit of the particulate hemp measured on the respective unit in any direction since the unit may be of a variety of shapes. That is, the maximum dimension of each hemp unit is averaged for all of the hemp units belonging to the particular category comprising the units. Moreover, any reference to sizing of hemp particles, hemp fines, hemp pellets, hemp crumbs, hemp cubes, or hemp briquettes hereinafter may be understood similarly to the aforementioned understanding of average dimension.

The understanding of "average piece dimension" or "average particle dimension" hereinafter is similar to that of 'average dimension'.

In one instance, the step of processing the particulate hemp, after the step of reducing the particulate hemp in size so as to lie in the first range, additionally includes further altering the particulate hemp in size such that the particulate hemp comprises an average dimension between 0.5 microns and 3.20 centimeters. In another instance, the step of processing the particulate hemp, after the step of reducing the particulate hemp in size so as to lie in the first range, additionally includes further altering the particulate hemp in size such that the particulate hemp comprises an average dimension between 0.8 microns and 3.00 centimeters. In a further instance, the step of processing the particulate hemp, after the step of reducing the particulate hemp in size so as to lie in the first range, additionally includes further altering the particulate hemp in size such that the particulate hemp comprises an average dimension between 0.9 microns and 2.80 centimeters.

In one arrangement, the step of processing the particulate hemp, after the step of reducing the particulate hemp in size so as to lie in the first range, may additionally include further reducing the particulate hemp in size so as to lie in a second range between 0.5 microns and 300 microns. Alternatively, the second range of the step of further reducing the particulate hemp in size, which comes after the step of reducing the particulate hemp in size so as to lie in the first range, may be between 0.8 microns and 250 microns. The second range of the step of further reducing the particulate hemp in size, which comes after the step of reducing the particulate hemp in size so as to lie in the first range, may also alternatively be between 0.9 microns and 200 microns.

The step of reducing the particular hemp in size so as to lie in the second range such as that between 0.5 microns and 300 microns may be performed using a hammer mill.

In one arrangement, the step of processing the particulate hemp, after the step of reducing the particulate hemp in size so as to lie in the first range, further includes binding together the particulate hemp into a prescribed size range between 0.60 centimeters and 3.20 centimeters. Alternatively, the prescribed size range of the step of binding together the particulate hemp may be between 0.80 centimeters and 3.00 centimeters. The prescribed size range of the step of binding together the particulate hemp may also alternatively be between 1.00 centimeters and 2.80 centimeters. The prescribed size range of the step of binding together the particulate hemp may also alternatively be between 1.20 centimeters and 2.60 centimeters.

The step of binding together the particulate hemp into the prescribed size range such as that between 0.60 centimeters and 3.20 centimeters may be performed using a pellet mill.

In one arrangement, the step of processing the particulate hemp, after the step of binding together the particulate hemp into the prescribed size range such as that between 0.60 centimeters and 3.20 centimeters, additionally includes reducing the particulate hemp in size so as to lie in a prescribed range between 0.30 centimeters and 2.80 centimeters. The prescribed range of the step of reducing the particulate hemp in size, which comes after the step of binding together the particulate hemp, may alternatively be between 0.50 centimeters and 2.60 centimeters. Alternatively, the prescribed range of the step of reducing the particulate hemp in size, which comes after the step of binding together the particulate hemp, may be between 0.50 centimeters and 2.60 centimeters. The prescribed range of the step of reducing the particulate hemp in size, which comes after the step of binding together the particulate hemp, may also alternatively be between 0.75 centimeters and 2.30 centimeters. The prescribed range of the step of reducing the particulate hemp in size, which comes after the step of binding together the particulate hemp, may also alternatively be between 1.00 centimeters and 2.00 centimeters.

The step of reducing the particulate hemp in size so as to lie in the prescribed range such as that between 0.30 centimeters and 2.80 centimeters is performed using a roller mill.

Optionally, the step of binding together the particulate hemp includes adding moisture to the particulate hemp at a beginning or throughout said step of binding together the particulate hemp so as to aid in binding the particulate hemp.

Preferably, the step of processing the particulate hemp, after the step of binding together the particulate hemp, further includes a step of cooling the particulate hemp.

In one arrangement, the step of processing the particulate hemp, after the step of binding together the particulate hemp, further includes a step of separating inadequate hemp units from the particulate hemp, the inadequate hemp units having an average dimension sized outside the prescribed size range such as that between 0.60 centimeters and 3.20 centimeters. In one instance, the step of removing the inadequate hemp units comprises applying suction to the particulate hemp to separate therefrom the inadequate hemp units that are sized smaller than said prescribed size range such as that between 0.60 centimeters and 3.20 centimeters.

In one arrangement, the step of processing the particulate hemp, after the step of reducing the particulate hemp in size so as to lie in the prescribed range such as that between 0.30 centimeters and 2.80 centimeters, additionally includes a step of separating inadequate hemp units from the particulate hemp, the inadequate hemp units having an average dimension sized outside said prescribed range such as that between 0.30 centimeters and 2.80 centimeters. In one instance, the step of removing the inadequate hemp units comprises applying suction to the particulate hemp to separate therefrom the inadequate hemp units that are sized smaller than said prescribed range such as that between 0.30 centimeters and 2.80 centimeters.

In certain consumer products for which hemp is suitable such as animal litter and bedding, it is desirable that the litter or bedding is free of dust which may be defined by the inadequate hemp units removed by suction.

Additionally or alternatively to applying suction, the step of removing the inadequate hemp units may comprise screening the particulate hemp. Preferably, the step of screening comprises a first separating step segregating or removing the inadequate hemp units which are larger than the respective range and a second separating step segregating or removing the inadequate hemp units which are smaller than the respective range.

Typically, the inadequate hemp units removed by suction are defined by the particulate hemp which was not properly pelletized. Also, these inadequate hemp units, which are removed by suction, may be defined by fines generated during the step of reducing the particulate hemp in size so as to lie in the prescribed range such as that between 0.30 centimeters and 2.80 centimeters. The suction may be applied to the particulate hemp in addition to the screening, and the suction may be applied during or after the screening of the particulate hemp.

It is preferred that the step of processing the particulate hemp, after the step of separating inadequate hemp units, includes reforming the inadequate hemp units back into the particulate hemp that is sized in the prescribed size range such as that between 0.60 centimeters and 3.20 centimeters by reiterating each one of (i) the step of reducing the particulate hemp in size into the first range, and (ii) the step of binding together the particulate hemp on said inadequate hemp units. The step of reforming the inadequate hemp units back into the particulate hemp augments efficiency of the method and affords very near 100% of the whole hemp stalks to be used, with little to no portion of the stalks wasted.

Preferably, the method, after the step of reducing the whole hemp stalks into particulate hemp, further comprises a step of mixing the particulate hemp so as to produce a blend of the particulate hemp which has a substantially uniform distribution of moisture. The step of mixing allows for the particulate hemp to be substantially uniformly moist prior to later size alteration steps of the step of processing.

In one instance, the step of providing the whole hemp stalks comprises providing bales thereof and the step of reducing the whole hemp stalks into particulate hemp comprises reducing the bales of the whole hemp stalks into the particulate hemp.

Preferably, the whole hemp stalks have a moisture content less than 15% by weight.

If moisture content of the whole hemp stalks is unsuitably high, in one instance the method, prior to the step of reducing the whole hemp stalks into particulate hemp, further comprises a step of drying the whole hemp stalks so that the whole hemp stalks have a moisture content less than 15% by weight.

In one arrangement, the method, after the step of processing the particulate hemp, further comprises a step of storing the particulate hemp in a manner suitable for selling the particulate hemp as or in a final product.

According to another aspect of the invention there is provided a system of processing whole hemp stalks into particulate hemp, wherein the whole hemp stalks have been harvested and each of the whole hemp stalks includes bast fiber and shive, the system comprising:

a preliminary size reduction stage arranged for reducing the previously harvested whole hemp stalks into particulate hemp, which is smaller in size than the whole hemp stalks and still includes bast fiber and shive;

a processing stage arranged for processing the particulate hemp and which includes:

a first size reduction station arranged for reducing the particulate hemp in size so as to lie in a first range between 25 microns and 500 microns;

wherein the particulate hemp includes bast fiber and shive throughout the processing stage.

The whole hemp stalks comprise bast fiber and shive. In the embodiment as described hereinafter, the system is able to form the particulate hemp from the whole hemp stalks without separating the bast fiber and shive. Thus, the system may be more efficient in processing whole hemp stalks as compared to prior art systems for doing same.

The first size reduction station may comprise a hammer mill.

In one instance, the preliminary size reduction stage is arranged for reducing the whole hemp stalks to the particulate hemp such that the particulate hemp has an average dimension between 1.10 centimeters and 7.70 centimeters. In another instance, the preliminary size reduction stage is arranged for reducing the whole hemp stalks into the particulate hemp such that the particulate hemp has an average dimension between 1.30 centimeters and 6.40 centimeters. In a further instance, the preliminary size reduction stage is arranged for reducing the whole hemp stalks into the particulate hemp such that the particulate hemp has an average dimension between 1.50 centimeters and 5.30 centimeters.

The preliminary size reduction stage may comprise a shredder, such as an agricultural shredder.

In one instance, the processing stage, after the first size reduction station, additionally includes a further size alteration stage which is arranged for altering the particulate hemp in size such that the particulate hemp has an average dimension between 0.5 microns and 3.20 centimeters. In another instance, the processing stage, after the first size reduction station, additionally includes a further size alteration stage which is arranged for altering the particulate hemp in size such that the particulate hemp has an average dimension between 0.8 microns and 3.00 centimeters. In a further instance, the processing stage, after the first size reduction station, additionally includes a further size alteration stage which is arranged for altering the particulate hemp in size such that the particulate hemp has an average dimension between 0.9 microns and 2.80 centimeters.

In one arrangement, the processing stage, after the first size reduction station, additionally includes a second size reduction station which is arranged for further reducing the particulate hemp in size so as to lie in a second range between 0.5 microns and 300 microns. Alternatively, the second range of the second size reduction station may be between 0.8 microns and 250 microns. The second range of the second size reduction station may also alternatively be between 0.9 microns and 200 microns.

The second size reduction station may comprise a hammer mill.

In one arrangement, the processing stage, after the first size reduction station, additionally includes a pelletizing station arranged for binding together the particulate hemp into in a prescribed size range between 0.60 centimeters and 3.20 centimeters. Alternatively, the prescribed size range of the pelletizing station may be between 0.80 centimeters and 3.00 centimeters. The prescribed size range of the pelletizing station may also alternatively be between 1.00 centimeters and 2.80 centimeters. The prescribed size range of the pelletizing station may also alternatively be between 1.20 centimeters and 2.60 centimeters.

In one arrangement, the processing stage, after the pelletizing station, additionally includes another size reduction station arranged for reducing the particulate hemp in size so as to lie in a prescribed range between 0.30 centimeters and 2.80 centimeters. Alternatively, the prescribed range of said another size reduction station may be between 0.50 centimeters and 2.60 centimeters. The prescribed range of said another size reduction station may also alternatively be between 0.75 centimeters and 2.30 centimeters. The prescribed range of said another size reduction station may also alternatively be between 1.00 centimeters and 2.00 centimeters.

Said another size reduction station, which is arranged for reducing the particulate hemp in size so as to lie in the prescribed range such as between 0.30 centimeters and 2.80 centimeters, may comprise a roller mill. For example, the roller mill may have counter-rotating rollers arranged for crushing the particulate hemp from the prescribed size range such as that between 0.60 centimeters and 3.20 centimeters into the prescribed range such as that between 0.30 centimeters and 2.80 centimeters.

Optionally, the pelletizing station is also arranged for adding moisture to the particulate hemp so as to aid in binding of the particulate hemp at the pelletizing station.

Preferably, the pelletizing station is also arranged for cooling the particulate hemp at a conclusion of the pelletizing station.

In one arrangement, the processing stage, after the pelletizing station, further includes a separation station arranged for segregating inadequate hemp units from the particulate hemp where the inadequate hemp units have an average dimension sized outside the prescribed size range between 0.60 centimeters and 3.20 centimeters.

In one instance, the separation station comprises a suction station arranged for applying suction to the particulate hemp to separate therefrom the inadequate hemp units that are sized smaller than said prescribed size range such as that between 0.60 centimeters and 3.20 centimeters.

In one arrangement, the processing stage, after said another size reduction station for reducing the particulate hemp in size so as to lie in the prescribed range such as that between 0.30 centimeters and 2.80 centimeters, additionally includes a separation station arranged for segregating inadequate hemp units from the particulate hemp where the inadequate hemp units have an average dimension sized outside the prescribed range such as that between 0.30 centimeters and 2.80 centimeters.

In one instance, the separation station comprises a suction station arranged for applying suction to the particulate hemp to separate therefrom the inadequate hemp units that are sized smaller than said prescribed range such as that between 0.30 centimeters and 2.80 centimeters.

Additionally or alternatively to the suction station, in one arrangement the separation station comprises a screening station arranged for screening the particulate hemp.

The suction station may be integrated with the screening station such that the suction is applied during the screening. Alternatively, the suction station may be independent of the screening station and come thereafter in the processing stage such that the suction is applied after the screening has been performed.

It is preferred that the system includes a conveyor arranged to transfer the inadequate hemp units from the separation station to a start of the processing stage for reforming the inadequate hemp units back into the particulate hemp sized in the prescribed size range such as that between 0.60 centimeters and 3.20 centimeters.

Preferably, the system includes an initial mixing station at a start of the processing stage that is arranged for mixing the particulate hemp so as to produce a blend of the particulate hemp which has a substantially uniform distribution of moisture.

In one instance, the preliminary size reduction stage is arranged to accept bales of the whole hemp stalks.

When the preliminary size reduction stage is arranged to accept the bales of the whole hemp stalks, the preliminary size reduction stage is preferably arranged for reducing the bales of the whole hemp stalks into the particulate hemp.

In one instance, the system also comprises a preliminary drying stage before the preliminary size reduction stage that is arranged for drying the whole hemp stalks so as to have a moisture content less than 15% by weight.

In one instance, the system includes a holding stage after the processing stage that is arranged for storing the particulate hemp in a manner suitable for sale as or in a final product.

In one instance, the system includes a conveyor operatively coupled between the preliminary size reduction stage and the processing stage.

According to another aspect of the invention there is provided a method of processing whole hemp stalks at a single location, each whole hemp stalk including bast fiber and shive, the method comprising:

providing the whole hemp stalks at said location;

using a shredder at said location, reducing the whole hemp stalks into particulate hemp which is smaller in size than the whole hemp stalks and still includes bast fiber and shive;

at said location, processing the particulate hemp without separating bast fiber and shive including:
  reducing the particulate hemp in size so as to lie in a first range between 25 microns and 500 microns so as to be usable for further processing of the particulate hemp into one of a plurality of different products each with different size;
  and using the particulate hemp sized in the first range as input to said further processing so as to derive a selected one of said plurality of different products;

wherein the particulate hemp includes unseparated bast fiber and shive throughout the step of processing the particulate hemp.

According to another aspect of the invention there is provided a system of processing whole hemp stalks into particulate hemp at a single location, wherein the whole hemp stalks have been harvested and each of the whole hemp stalks includes bast fiber and shive, the system comprising:

a shredder arranged at said location for reducing the previously harvested whole hemp stalks into particulate hemp, which is smaller in size than the whole hemp stalks and still includes bast fiber and shive;

a processing stage arranged at said location for processing the particulate hemp without separating bast fiber and shive that includes:
  a first size reduction station arranged for reducing the particulate hemp in size so as to lie in a first range between 25 microns and 500 microns so as to be usable for further processing of the particulate hemp into one of a plurality of different products each with different size;
  at least one further size alteration station receiving the particulate hemp sized in the first range as input thereto for said further processing so as to derive a selected one of said plurality of different products;

wherein the particulate hemp includes unseparated bast fiber and shive throughout the processing stage.

According to a further aspect of the invention there is provided a method of obtaining cannabinoid oil from processed hemp comprising:

receiving the processed hemp, which has been processed from a whole hemp stalk to a particulate form having reduced size;

extracting the cannabinoid oil from the processed hemp using a fluid extraction process in which an extracting solvent is applied to the processed hemp;

wherein the received processed hemp is characterized in that it has been previously pelletized as part of its processing from the whole hemp stalk to the particulate form.

In the embodiment as described in more detail hereinafter, very low strains of tetrahydrocannabinol (THC) and higher strains of cannabidiol are preferably sought and these are obtained by starting with a raw material which has these characteristics, that is the raw material is preferably low in THC and high in cannabidiol. Therefore, appropriate strains of hemp plant are chosen to meet such requirements.

Preferably, when the processed hemp is received from another external facility, the processed hemp is bagged at the other external facility so as to prevent the processed hemp from drying out before the method for obtaining the cannabinoid oil is carried out.

Preferably, the whole hemp stalk, from which the processed hemp is formed, was harvested when the hemp plant was in flower before seed had formed. As such, the processed hemp does not contain any hemp seed.

Preferably, the processed hemp includes leaves and flower buds of the harvested whole hemp stalk.

Preferably, the processed hemp includes bast fiber and shive of the harvested whole hemp stalk.

Preferably, the harvested whole hemp stalk, from which the processed hemp is formed, was left to dry outdoors (typically in the field) after being cut but prior to being processed into the processed hemp.

Suitable fluid extraction processes include carrier oil extraction, super- or sub-critical carbon dioxide ($CO_2$) extraction, or solvent extraction (an example of a solvent conventionally associated therewith is grain alcohol, butane, and hexane). These examples form part of the category of processes including liquid-liquid extraction which can also be referred to as solvent extraction.

Preferably, the harvested whole hemp stalk is of the variety having higher levels of cannabidiol than tetrahydrocannabinol.

In one arrangement, the step of extracting the cannabinoid oil includes generating used processed hemp deprived of the cannabinoid oil initially contained therein. The aforementioned extraction arrangement comprising the pressurized fluid may be better suited for generating the used processed hemp that is still usable in or as a vendible product as compared to an extraction arrangement using pressing which crushes the subject material.

Preferably, a step of drying the used processed hemp so as to be suited for use as or in a salable product.

Preferably, the processed hemp comprises an average dimension between 0.5 microns and 50 centimeters. Such sizing may make the processed hemp better suited for transportation between facilities.

All or any of the above features may be combined with one another.

BRIEF DESCRIPTION OF THE DRAWINGS

One embodiment of the invention will now be described in conjunction with the accompanying drawings in which.

In the drawings like characters of reference indicate corresponding parts in the different figures.

DETAILED DESCRIPTION

Figure 1:
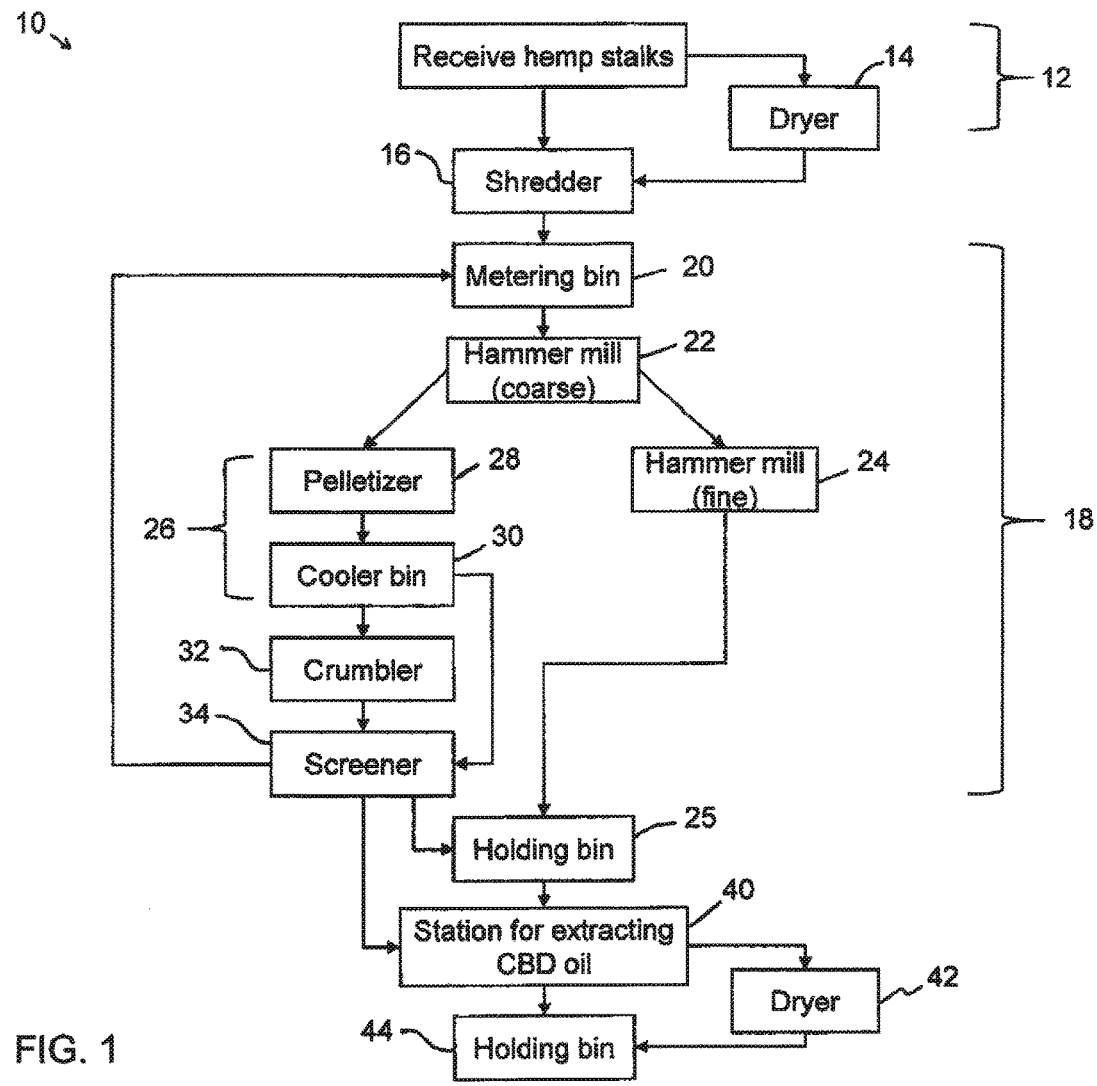
FIG. 1 is a flow diagram of a system for processing whole hemp stalks.
Figure 2:
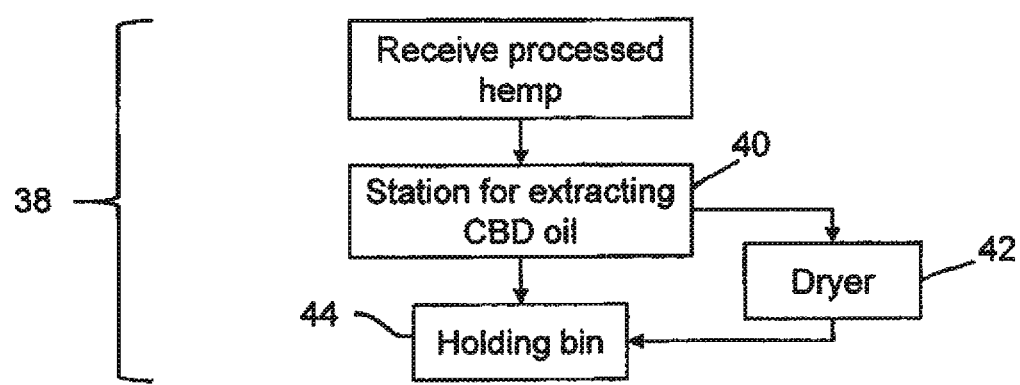
FIG. 2 is a flow diagram of a system of processing particulate hemp for extracting cannabinoid oil therefrom.

Referring to the accompanying figures, there is illustrated a system for processing whole hemp stalks that is generally indicated by reference numeral 10. The system 10 is configurable to produce one of hemp fines or flour, hemp pellets, and hemp crumbs. Each of the hemp fines, pellets, and crumbs define particulate forms of hemp stalk. Each of the particulate forms are produced from whole hemp stalks such that the fines, pellets, and crumbs maintain characteristics of the hemp stalk and differ in terms of physical size.

The system 10 commences with a receiving stage 12 for receiving the whole hemp stalks. Typically, the whole hemp stalks are delivered in the form of round or square bales. At the receiving stage, weight and moisture content of the bales is determined. Preferably, the whole hemp stalks have a moisture content in a range between 12% and 15% by weight; however, the moisture content may be below this range and the hemp stalks may still be suited for processing into the particulate hemp. Any one of the bales which have moisture content exceeding 15% by weight may be rejected; alternatively, these bales that define excessively moist whole hemp stalks may be passed through a preliminary drying station 14 arranged for drying the bales. When the bales are passed to the preliminary drying station, the bales are dried until the moisture content thereof is less than 15% by weight which defines an upper range limit for acceptable moisture content.

After the receiving stage 12, the bales are transferred to a cutting stage 16 which performs a step of cutting the whole hemp stalks into hemp pieces smaller than the whole hemp stalks. The cutting stage comprises a shredding station 16 which produces the hemp pieces sized to have an average piece dimension in a prescribed piece range which is preferably between 1.50 centimeters and 5.30 centimeters. Alternatively, the prescribed piece range may be between 1.30 centimeters and 6.40 centimeters and provide comparable results to the preferred prescribed piece range. The prescribe piece range may also be between 1.10 centimeters and 7.70 centimeters and provide comparable results to the preferred prescribed piece range. The preferred prescribed piece range of the average piece dimension is analogous to a typical, average dimension of mulch for use in landscaping or gardening. In the illustrated embodiment, the shredding station comprises an agricultural shredder which has a body and a rotor rotatably carried within the body. The body includes at least one stationary counter knife supported in the body. The rotor, which is made of steel, supports counter shredding blocks. Each shredding block is sized to be 40 millimeters by 40 millimeters by 20 millimeters. The hemp stalks are shredded between the rotor and the at least one stationary counter knife. Further to the rotor and the counter knife, the shredder comprises a screen locating openings for passing the hemp pieces therethrough once the hemp stalks are cut into sufficiently small portions. The openings are selectively sized to transfer out of the shredder the portions of the hemp stalks which are sized in the prescribed piece range mentioned hereinbefore. Size of the openings may be adjusted depending on the average piece dimension within the prescribed piece range that is desired. The shredder may be capable of performing the step of cutting the hemp stalks at a processing or cutting rate of 4,000 pounds per hour; however, in other embodiment the shredder may have a cutting rate less than that of the illustrated embodiment and still yield comparable results to that of the illustrated embodiment. Such agricultural shredders are known in the art and thus are not illustrated in detail herein. Note that the hemp pieces include bast fiber and hurds collectively defining shive of the whole hemp stalks. As such, the shredding station 16 is arranged to cut through the bast fibers in order to form the hemp pieces. Further to the bast fiber and the hurds, the hemp pieces may also include leaves or flower buds of the hemp stalk.

Once the whole hemp stalks have been reduced to the hemp pieces, the hemp pieces are transferred to a size reduction stage 18 which performs a step of granulating the hemp pieces into the particulate hemp. The size reduction stage is configured so as to produce one of the hemp fines, the hemp pellets, and the hemp crumbs. The size reduction stage may produce the particulate hemp defined by one of the hemp fines, pellets, or crumbs having an average particle dimension between 0.5 microns and 3.20 centimeters. First, the stations which are common to each one of the hemp products produced by the system 10 are discussed.

At a start of the size reduction stage, the hemp pieces are transferred from the shredding station 16 to a mixing station 20 which performs a step of mixing the hemp pieces so as to produce a blend of the hemp pieces which has a substantially uniform distribution of moisture. Typically, the moisture content of the bales is contained closer to outer faces of the respective bale. Thus, the step of mixing the hemp pieces ensures that the blend of hemp pieces has uniform moisture content, and this blend is then converted to one of the hemp products. In the system of the illustrated embodiment, the mixing station comprises a metering bin 20. It will be appreciated that the mixing station can be considered to be part of either one of the cutting stage 16 or size reduction stage 18; alternatively, the mixing station 20 can be considered as independent of either one of the cutting or size reduction stages so long as the mixing station is intermediate the shredding station 16 and a coarse granulating station 22 of the size reduction stage.

The size reduction stage comprises the coarse granulating station 22 which is common to each configuration of the illustrated embodiment. The coarse granulating station 22 performs a coarse pulverizing step which reduces the hemp pieces to hemp particles sized in a first granule range which is preferably between 75 microns and 400 microns. Alternatively, the first granule range may be between 25 microns and 500 microns and provide comparable results to that of the preferred first granule range. Size of the hemp fines is analogous to that of sawdust. In the system 10 of the illustrated embodiment, the coarse granulating station comprises a coarse hammer mill.

To produce the hemp fines, the hemp particles are transferred from the coarse granulating station 22 to a fine granulating station 24 which performs a fine pulverizing step for further reducing the hemp particles into hemp fines. The hemp fines are sized in a second granule range which is preferably between 0.9 microns and 200 microns. Alternatively the second granule range may be between 0.8 microns and 250 microns and provide comparable results to that of the preferred second granule range. The second granule range may also be between 0.5 microns and 300 microns and provide comparable results to that of the preferred second granule range. In the illustrated embodiment, the fine granulating station 24 comprises a fine hammer mill which is arranged to grind the hemp particles more finely than the coarse hammer mill of the coarse granulating station. As such, the hemp fines contain the bast fiber and the hurds of the hemp stalks. If the hemp stalks also included the leaves and flower buds, the hemp fines also include the leaves and flower buds thereof albeit in portions. The hemp fines define one form of the particulate hemp which is produced by the system of the illustrated embodiment. The hemp fines or flour can then be bagged in a manner suitable for storage or in a manner suitable for sale in or as a consumer product. Alternatively, the hemp fines may be transferred to a storage station 25 which will be described later in more detail.

To produce either one of the hemp pellets or the hemp crumbs, the hemp particles are transferred from the coarse granulating station 22 to a pelletizing station 26 which performs a pelletizing step. In the pelletizing step, the hemp particles are formed into hemp pellets sized in a pellet range which is preferably between 1.20 centimeters and 2.60 centimeters. Alternatively the pellet range may be between 1.00 centimeters and 2.80 centimeters and provide comparable results to that of the preferred pellet range. The pellet range may also be between 0.60 centimeters and 3.20 centimeters and provide comparable results to that of the preferred pellet range. In the system of the illustrated embodiment, the pelletizing station 26 comprises a pellet mill or pelletizer 28. One example of the pellet mill that is appropriate for producing the hemp pellets sized in the desired pellet range has the following parameters, as understood by a person with normal skill in the art: (i) die diameter of 26"; (ii) hole diameter of ¼"; (iii) effective thickness of 2⅛; (iv) relief of ¹³⁄₁₆; and (v) operating temperature of 190 degrees Fahrenheit to 205 degrees Fahrenheit (operating at 200 degrees Fahrenheit is preferred). In some instance where the moisture content of the hemp particles is too low such that the hemp particles do not bind together in the pelletizing step, moisture typically comprising steam or water is added to the hemp particles in the pelletizing station so as to aid in forming the hemp pellets. The hemp pellets still contain the bast fiber and the hurds of the hemp stalks. If the hemp stalks also included the leaves and flower buds, the hemp pellets also include the leaves and flower buds thereof albeit in portions.

Since formation of the hemp pellets involves high temperatures, the hemp pellets are transferred to a cooling station 30 belonging to the pelletizing station. The cooling station performs a step of cooling the hemp pellets such that the hemp pellets harden. The cooling station comprises a cooler bin 30 in the system of the illustrated embodiment.

To produce the hemp crumbs or crumbles, the hemp pellets are transferred from the cooling station 30 to a crushing station 32 which performs a crushing step. In the crushing step, the hemp pellets are reduced to hemp crumbs sized in a crumb range which is preferably between 1.00 centimeters and 2.00 centimeters. Alternatively, the crumb range may be between 0.75 centimeters and 2.30 centimeters and provide comparable results to that of the preferred crumb range. The crumb range may also be between 0.30 centimeters and 2.80 centimeters and provide comparable results to that of the preferred crumb range. In other embodiments, the crumb range may lie between 0.03 centimeters and 0.65 centimeters depending on intended applications of the crumbs. In the system of the illustrated embodiment, the crushing station comprises a roller mill 32; however, in alternative embodiments the crushing station comprises a hammer mill separate from the hammer mill 22 of the coarse granulating station. The crushing station may also be referred to as a crumbler which forms the hemp crumbs or crumbles. The hemp crumbs still contain the bast fiber and the hurds of the whole hemp stalks. As such, some of the bast fiber which is difficult to break may remain such that some hemp crumbs are similar in size to the respective hemp pellets because the respective crumbs are held together by strands of the fiber even after grinding or crushing the hemp pellets. Additionally, if the hemp stalks also included the leaves and flower buds, the hemp crumbs also include the leaves and flower buds thereof albeit in portions.

Regardless of whether the system is configured to produce the hemp pellets or the hemp crumbs, in both instances the particulate hemp defined thereby is transferred to a screening station 34 of the size reduction stage for removing hemp pellets or bad hemp crumbs that have an average unit dimension lying outside the respective one of the pellet range or the crumb range depending on which hemp product is being produced; these hemp pellets or crumbs define inadequate or bad hemp units. The bad hemp pellets or crumbs are transferred to a start of the size reduction stage 18 so as to pass through the coarse granulating station 22 and pelletizing station 26 a subsequent time. In the illustrated embodiment, the bad hemp units are transferred back to the mixing station 20 instead of being transferred directly back to one of the coarse granulating station 22 or the pelletizing station 26. The mixing station typically has sufficient capacity to accept additional material for processing, while the coarse granulating station and pelletizing station are typically near full capacity. In alternative embodiments comprising granulating and pelletizing stations of greater capacity, the bad hemp units can be transferred to either one of these stations in lieu of the mixing station.

The bad hemp units which exceed the allowed range are first separated from acceptable hemp units having the average unit dimension which lies within the respective range. In the illustrated embodiment, the first separation step is performed by a first screen which allows the acceptable hemp units to pass through openings located in the first screen. For example, the first screen has openings sized at the upper range limit of the pellet or crumb range. A second separation step performed by a second screen separates the bad hemp units that have the average unit dimension below the respective range. The bad hemp units segregated by the second screen include dust defined by the hemp particles that were not properly pelletized in the pelletizing station. In the case of the hemp crumbs, the dust may also be defined by fines generated during crushing of the hemp pellets to form the hemp crumbs. For example, the second screen locates openings sized at the lower range limit of the pellet or crumb range so that the bad hemp units that are below the lower range limit of the respective range pass through the openings. In another example, the openings of the second screen are 4 mm in diameter. In addition to the screens, a suction station separates the dust from the particulate hemp by applying suction to the particulate hemp. The suction station comprises a vacuuming apparatus. The suction can be applied during the second separation step; alternatively the suction can be applied after the second separation step has been performed. Once the dust has been removed from the particulate hemp, the bad hemp units are transferred to the start of the size reduction stage. The screening station and suction station collectively define a separating station for segregating the bad hemp units from the particulate hemp.

Overall, the system 10 is capable of processing 2 tonnes to 2.5 tonnes of whole hemp stalk per hour.

After the separation or segregation station, the hemp pellets and crumbs that are acceptably sized are transferred to the storage station 25. At the storage station, a portion of the particulate hemp is stored in a manner suitable for selling as a consumer product or for use in a consumer product. Another portion of the particulate hemp is stored so as to be prepared for loading for transportation to a separate oil extraction facility 38 which performs a step of extracting cannabinoid (CBD) oil from the particulate hemp. In other embodiments, the particulate hemp may be loaded directly onto a vehicle such as a tanker for transportation (i.e., by road) to the oil extraction facility. The transportation arrangement may also include train (i.e., by rail) and ship (i.e., by water). In further embodiments, a facility comprising the system 10 may also include subsequent stages and/or stations 40 for performing the step of extracting the CBD oil; as such, the particulate hemp may be transferred directly to the appropriate oil extraction stages and/or stations after the screening station.

Similarly to the hemp crumbs and pellets, the hemp fines may also be stored in preparation for transfer to the oil extraction facility for extracting oil from the hemp fines.

Furthermore, it will be appreciated that the term 'particulate hemp', especially as the term pertains to the concept of oil extraction, is broadened to be understood as processed hemp. 'Processed hemp' refers to a smaller forms (i.e., relating to physical size) reduced in size from the hemp stalks such that the smaller forms are easier to transport. Thus, the processed hemp may include the hemp fines, hemp pellets, and hemp crumbs that are sized as described hereinbefore. The processed hemp may also include hemp cubes and hemp briquettes. The hemp cubes are sized typically in a cube range between 1.20 centimeters and 7.70 centimeters so as to be larger than or similarly sized as the hemp pellets. The hemp cubes may be produced from the hemp stalks in a similar fashion to the hemp pellets produced by the system 10. That is, in other embodiments the pelletizing station 26 or the pelletizer 28 may be replaced with similar equipment so as to produce the cubes which are cubic in form instead of the hemp pellets which may be of varying shapes. The processed hemp may also include hemp briquettes which are sized larger than the hemp cubes so as to be in a briquette range typically between 5 centimeters and 50 centimeters. In other embodiments, the system 10 may be configured to produce the hemp briquettes such that the pelletizing station 28 or pelletizer is replaced with a briquetting station or briquetting machine, respectively. Additionally, the processed hemp may include all or any combination of the constituent components of the hemp stalks including the bast fiber, the hurds, the leaves, and the flower buds. Typically, inclusion of the leaves or the flower buds of the hemp stalks may augment an amount of CBD oil contained in the processed hemp. Also, using different strains of hemp may yield different amounts of CBD oil in the processed hemp.

Returning to the extraction of the CBD oil, the step of extracting the CBD oil typically generates used particulate hemp which is deprived of the CBD oil initially contained therein. Typically, the used particulate hemp has moisture content which is greater than that suited for consumer products such as animal litter, animal bedding, and absorbency products. Thus, the used particulate hemp is dried in a drying station 42 so as to be suited for use in the consumer products like those mentioned hereinbefore. Typically, the step of drying the used particulate hemp is performed with heat and air. The used particulate hemp may then be stored in a storage station 44 similar to the storage station 25.

Tests commissioned by the applicant show that for at least one particular strain of hemp, the hemp pellets contain about 0.02% of CBD. Thus, the tests indicate that the processed hemp is not devoid of the CBD oil initially contained in the hemp stalks. As mentioned before, the content or amount of CBD oil in the processed hemp may be increased by using different strains of hemp and if the hemp stalks that are processed include the leaves or the flower buds.

It will be appreciated that the system of the illustrated embodiment may also be suited for other types of organic matter and crops.

It will also be appreciated that a particular shape of each one of the hemp products may vary so long as each individual particle of each hemp product fits within the corresponding size range.

It will also be appreciated that binding materials are not necessary to produce any one of the hemp fines, crumbs, or pellets in the system 10 of the illustrated embodiment.

The hemp products produced by the system 10 and corresponding method have many applications. The following are attributes of hemp may lend to its advantages in the applications which are mentioned later: (i) bast fiber length is 5 millimeters to 40 millimeters in length; (ii) primary bast fibers, which may be most favourable for certain applications, are long and low in lignin content; (iii) secondary bast fibers, which are secondary to the primary fibers for the certain applications, are shorter than the primary bast fibers and high in lignin content; and (iv) tertiary bast fibers, which are third to the primary fibers for the certain applications, are shorter than the secondary bast fibers and high in lignin content. Also, hemp comprises cellulose typically in a range between 32% and 38%.

Hemp is suited for a number of consumer products such as animal lifter (e.g., cat litter); animal bedding for animals like horses, birds, snakes, and rabbits; absorbing or absorption products suited for use in spills comprising oil, gas, chemicals considered hazardous and/or having adverse effects on humans and the environment, sewage, and water; absorption products for absorbing gases generated by sewer tanks or ponds; and 3D printing filament or molding when the hemp is combined with plastic material.

In particular, the hemp pellets and hemp crumbs are suitable for use in animal litter for domestic pets such as cats, birds, and horses because these hemp products provide desirable characteristics suited for the animal litter including (i) rapidly and efficiently absorbing animal excretions; (ii) ability to rapidly minimize unpleasant odors; (iii) non-adherence to animal paws and fur; (iv) biodegradability; and (v) low cost.

The hemp pellets and hemp crumbs, when made from hemp having low tetrahydrocannabinol (THC) content, also provide the following characteristics desirable in the animal litter such as (i) ability to inhibit the growth of microorganisms; (ii) ability to repel insects and pests such as fleas and moths; (iii) little to no dust content; and (iv) sufficiently low levels of psychoactive chemicals so as to not produce physical or psychological effects. Moreover, since animal litter is widely used, it is important that the material from which the litter is made is environmentally friendly. Hemp may be grown without application of insecticides or pesticides so that hemp is 100% organic the hemp, thereby meeting one of the preferred requirements of animal litter.

Additionally, the hemp products produced by the system 10 have characteristics including (i) high absorbency; and (ii) ability to rapidly minimize unpleasant odors. Thus, the hemp fines and crumbs are suited for absorbing or absorption products. Generally speaking, hemp is able to absorb liquids up to 490% of its weight; however, the hemp fines are likely to absorb liquids more quickly than the hemp crumbs or the hemp pellets because the hemp fines are smaller in size than the crumbles or pellets, and the hemp crumbles are likely to absorb liquids more quickly than the hemp pellets because the crumbles are smaller in size compared to the pellets. Additionally, hemp is able to neutralize chemicals to a pH near 7. In chemical or oil spills, acid neutralization may afford the chemicals or the oil to be rendered less harmful to an external environment surrounding the spill. In animal litter as mentioned earlier, acid neutralization may afford neutralization of ammonia contained in animal excretions (especially in animal urine) so as to minimize an unpleasant smell of the ammonia.

The hemp crumbs or the hemp pellets may be blended with binders like corn or wheat starch to form an animal litter which is able to form clumps.

In another example, the hemp crumbs and pellets may also be suited for use as mulch. In a further example example, the hemp fines are suited for absorbing liquid such as in scenarios of water, oil, or chemical spills. In a yet further example, the hemp fines are suited for mixing with at least one of polypropylene, polyethylene, polyurethane, polylactic acid, PHA-green resin, and magnesium oxide for making plastic filament or for use in molding.

The hemp products produced by the system 10 may also be suited for use as or in loose fill insulation.

It will be appreciated that the hemp retains its desirable characteristics regardless of the physical form in the present embodiment, i.e., regardless of whether the hemp is in the form of the hemp fines, the hemp pellets, and the hemp crumbs. As such, the aforementioned qualities of one of the hemp product are likely maintained in another one of the hemp products produced by the system 10.

Hemp may also be suited for use as or in biomass.

Furthermore, hemp contains the CBD oil and the CBD oil contained in the hemp may be extracted without considerably affecting performance of the hemp for the consumer products mentioned hereinbefore.

The CBD oil is found in an upper portion of the plant such as in leaves and flower buds of the stalks. Typically, the CBD oil content in the hemp stalk ranges between 2% and 7%. It may be desirable to extract the CBD oil from the hemp stalks because the oil is suited for therapeutic use for a variety of diseases such as anxiety disorders, post-traumatic stress disorder, psychosis, epilepsy, dystonia, diabetes, cancer, inflammatory diseases, and skin diseases.

The hemp stalks from which the particulate hemp may be harvested differently depending on whether the hemp products derived from the hemp stalks are to be used primarily for such consumer products as those mentioned hereinbefore or primarily for oil extraction. In case of the latter, the hemp stalks may be harvested once the hemp stalks have flowered such that the CBD oil content in the stalks is higher than prior to or during flowering. In other cases, the hemp stalks may be harvested during flowering. Furthermore, depending on a state in which the hemp stalks are harvested a swather or combine harvester may be better suited for cutting the hemp stalks. After the hemp stalks are cut, the hemp stalks may be left outside in a field to dry until the hemp stalks have the proper moisture content. Once dried, the hemp stalks may be baled. Once baled, the hemp stalks may be covered under tarps or stored in a shed before sending the hemp stalks to a facility comprising the system 10 for processing.

In another arrangement of the present invention, the whole hemp stalks are harvested when the stalks are in full flower (full bloom/blossom) but before any seeds have formed in order to obtain economically suitable yields of CBD oil. This is because the hemp seeds do not contain the desired strain of cannabinoid used and therefore need not be present in the raw material, which is the processed hemp, from which the oil is later extracted. However, at the time of harvest, the whole hemp stalks do have flower buds (also known as blooms) and leaves, and these are not removed from the stalks so as to remain in the particulate processed hemp that is formed therefrom. Typically, when the stalks are destined for oil extraction, the whole hemp stalks are left in the field after cutting so as to dry to a moisture content between 10% and 18% by weight. Alternatively, drying to a moisture content between 10% and 14% or to that between 15% and 18% may be equally suitable. The hemp stalks are then baled once they have dried in the field, and subsequently the dried and baled hemp stalks are passed through the size alteration stages to form the particulate hemp that is later used in the oil extraction.

In some instances, separate facilities carry out each of the processing of the whole hemp stalks into particulate hemp and the oil extraction. The particulate processed hemp is bagged at a conclusion of its processing in the first facility so that the particulate hemp retains its moisture/oil content before the oil extraction is carried out. That is, the processed hemp is stored in a way suitable for shipping but in a closed arrangement (for example, closed bags or other sealed containers) such that the particulate hemp is prevented from drying out before the oil extraction. As such, the particulate form of the hemp, which is a consequence of its processing from a whole stalk state, by its significantly reduced size makes the hemp better suited for transport and better suited for holding in a moisture sealing/retaining arrangement.

At the oil extraction facility, a fluid extraction process is used to remove the oil from the processed hemp. That is, a suitable fluid (typically in liquid state) is applied as an extracting solvent to the processed hemp using suitable apparatus for carrying out the extraction. Typically, the processed hemp is carried in a first immiscible liquid such as water and is transferred to the extracting solvent by mixing together in the suitable apparatus. Vice versa, the extracting solvent may be first applied to the processed hemp and then mixed with another immiscible liquid so that the other immiscible liquid carries the desired CBD oil at the end of the process. The carrier liquid which contains the desired component at the end of the process is then removed from, and in this way the CBD oil is extracted.

A number of suitable such processes forming a category of processes known as liquid-liquid extraction or otherwise as solvent extraction are effective for extracting the desired strains of cannabinoids, and examples include supercritical fluid extraction (for example, using supercritical carbon dioxide), conventional solvent extraction (conventional extraction solvents associated therewith include, for example, grain alcohol or ethanol high grade alcohol), or carrier oil extraction (for example, using olive oil). Subcritical carbon dioxide ($CO_2$) extraction may also be suitable. These processes are known in the art in how they are applied to hemp and thus are not described in detail herein. Where possible, subcritical or supercritical $CO_2$ extraction is desirably used because this extraction process uses a chemical (i.e., $CO_2$) that is non-toxic and non-flammable as compared to the chemicals employed in solvent extraction (e.g., butane, grain alcohol, isopropyl alcohol, hexane, or ethanol). $CO_2$ extraction also retains beneficial plant waxes which are present and removes the chlorophyll from the end product. On the other hand, conventional solvent extraction is typically less expensive and may be easier to perform over supercritical $CO_2$ extraction. Note that the specifically chosen process for extracting the oil may vary depending on the end-use of the oil that is derived.

Based on presently known applications for oil derived from hemp, the strain of cannabinoid having gained in popularity is cannabidiol. Therefore, cannabidiol is the strain which is typically desired and therefore isolated from the hemp, although other cannabinoid strains may be extracted alternatively or additionally to cannabidiol.

As a result of the oil extraction process, used processed hemp is produced and it is deprived of the CBD oil initially contained therein. As such, in addition to other benefits provided by the respective extraction process, the fluid extraction processes mentioned above may be better suited for providing such used processed hemp that can still be used in or as a vendible product because these fluid extraction processes leave the physical form of the hemp substantially unaltered as compared to an extraction arrangement using pressing which crushes the subject material. That is, the fluid extraction processes remove the CBD oil without compromising other physical properties of the processed hemp which make it suitable for use in/as a salable product but which do not depend on presence of CBD oil in the hemp. The used processed hemp which will be used in/as the salable product is dried, for example by placing the used processed hemp in a heated storage chamber to let the hemp air-dry, so as to be suited for its subsequent use.

As described in detail hereinbefore, the harvested whole hemp stalks are processed into one of pellets, flour, and crumbles. Each of these products include both bast fiber and shive, which remain substantially intact throughout the processing stages, as well as the leaves and flower buds which augment the content of the desired CBD strains in the processed hemp. Although it is possible to extract CBD oil from the flour, the physical form of the pellets and crumbles may make them more manageable for extraction when compared to a powdery flour form as apparent above, and thus the pellets and crumbles are preferred for the oil extraction over the flour. As such, the processed hemp from which the oil is extracted has typically gone through a pelletizing step as part of its processing.

Furthermore, the processed hemp is generally preferred as the raw material for oil extraction over the original whole hemp stalks as the processed hemp is more suitably sized and each unit thereof contains a plurality of components of the original whole hemp stalk like the shive, bast fiber, leaves, and flowers (through the processing as described hereinbefore) such that uniform yields of the CBD oil may be produced in terms of quality and relative proportions of desired CBD strains in the oil. The same is not necessarily true if the whole hemp stalks, as harvested, were used as the raw material for oil extraction or even if the whole hemp stalks were separated into constituent parts of the plant and then used as the raw material.

Since various modifications can be made in my invention as herein above described, and many apparently widely different embodiments of same made, it is intended that all matter contained in the accompanying specification shall be interpreted as illustrative only and not in a limiting sense.

The invention claimed is:

1. A method of processing whole hemp stalks at a single location, each whole hemp stalk including bast fiber and shive, the method comprising:
providing the whole hemp stalks at said location;
at said location, reducing the whole hemp stalks into particulate hemp which is smaller in size than the whole hemp stalks and still includes bast fiber and shive;
at said location, processing the particulate hemp without separating bast fiber and shive including:
reducing the particulate hemp in size so as to lie in a first size range so as to be usable for further processing of the particulate hemp into one of a plurality of different products each with different size;
wherein the particulate hemp includes unseparated bast fiber and shive throughout the step of processing the particulate hemp.

2. The method according to claim 1 wherein the step of processing the particulate hemp, after the step of reducing the particulate hemp in size so as to lie in the first size range, additionally includes further reducing the particulate hemp in size so as to lie in a second size range comprising a range of smaller average dimensions of the particulate hemp than a range of average dimensions of the particulate hemp defined by the first size range.

3. The method according to claim 1 wherein the step of processing the particulate hemp, after the step of reducing the particulate hemp in size so as to lie in the first size range, further includes binding together the particulate hemp into a prescribed pellet size range comprising a range of larger average dimensions of the particulate hemp than a range of average dimensions of the particulate hemp defined by the first size range.

4. The method according to claim 3 wherein the step of processing the particulate hemp, after the step of binding together the particulate hemp, additionally includes reducing the particulate hemp in size so as to lie in a prescribed crumble size range comprising a range of larger average dimensions of the particulate hemp than the range of average dimensions of the particulate hemp defined by the first size range.

5. The method according to claim 3 wherein the step of binding together the particulate hemp includes adding moisture to the particulate hemp at a beginning or throughout said step of binding together the particulate hemp so as to aid in binding the particulate hemp.

6. The method according to claim 3 wherein the step of processing the particulate hemp, after the step of binding together the particulate hemp, further includes a step of cooling the particulate hemp.

7. The method according to claim 3 wherein the step of processing the particulate hemp, after the step of binding together the particulate hemp, further includes a step of separating inadequate hemp units from the particulate hemp, the inadequate hemp units respectively having an average dimension sized outside the prescribed pellet size range.

8. The method according to claim 4 wherein the step of processing the particulate hemp, after the step of reducing the particulate hemp in size so as to lie in the prescribed crumble size range, additionally includes a step of separating inadequate hemp units from the particulate hemp, the inadequate hemp units respectively having an average dimension sized outside the prescribed crumble size range.

9. The method according to claim 7 wherein the step of processing the particulate hemp, after the step of separating inadequate hemp units, includes reforming the inadequate hemp units back into the particulate hemp that is sized in the prescribed pellet size range by reiterating on said inadequate hemp units each one of (i) the step of reducing the particulate hemp in size so as to lie in the first size range, and (ii) the step of binding together the particulate hemp.

10. The method according to claim 1 wherein the step of providing the whole hemp stalks comprises providing bales thereof and the step of reducing the whole hemp stalks into particulate hemp comprises reducing the bales of the whole hemp stalks into the particulate hemp.

11. A system of processing whole hemp stalks into particulate hemp at a single location, wherein the whole hemp stalks have been harvested and each of the whole hemp stalks includes bast fiber and shive, the system comprising:
  a preliminary size reduction station arranged at said location for reducing the previously harvested whole hemp stalks into particulate hemp, which is smaller in size than the whole hemp stalks and still includes bast fiber and shive;
  a processing stage arranged at said location for processing the particulate hemp without separating bast fiber and shive, the processing stage including:
    a first size reduction station arranged for reducing the particulate hemp in size so as to lie in a first size range so as to be usable for further processing of the particulate hemp into one of a plurality of different products each with different size;
    at least one further size alteration station receiving the particulate hemp sized in the first size range as input thereto for said further processing so as to derive a selected one of said plurality of different products;
  wherein the particulate hemp includes unseparated bast fiber and shive throughout the processing stage.

12. The system according to claim 11 wherein said at least one further size alteration station is a second size reduction station which is arranged for further reducing the particulate hemp in size so as to lie in a second size range comprising a range of smaller average dimensions of the particulate hemp than a range of average dimensions of the particulate hemp defined by the first size range.

13. The system according to claim 12 wherein the second size reduction station comprises a hammer mill.

14. The system according to claim 11 wherein the first size reduction station comprises a hammer mill.

15. The system according to claim 11 wherein the preliminary size reduction stage comprises a shredder.

16. The system according to claim 11 wherein said at least one further size alteration station comprises a pelletizing station arranged for binding together the particulate hemp into a prescribed pellet size range comprising a range of smaller average dimensions of the particulate hemp than a range of average dimensions of the particulate hemp defined by the first size range.

17. The system according to claim 16 wherein said at least one further size alteration station, after the pelletizing station, further comprises another size reduction station arranged for reducing the particulate hemp in size so as to lie in a prescribed crumble size range comprising a range of larger average dimensions of the particulate hemp than the range of average dimensions of the particulate hemp defined by the first size range.

18. The system according to claim 17 wherein said another size reduction station, which is arranged for reducing the particulate hemp in size so as to lie in the prescribed crumble size range, comprises a roller mill.

19. The system according to claim 16 wherein the processing stage, after the pelletizing station, further includes a separation station arranged for segregating inadequate hemp units from the particulate hemp where the inadequate hemp units respectively have an average dimension sized outside the prescribed pellet size range.

20. The system according to claim 19 wherein the separation station comprises a suction station arranged for applying suction to the particulate hemp to separate therefrom the inadequate hemp units that are sized smaller than a lower limit of the prescribed pellet size range.

21. The system according to claim 19 wherein the separation station comprises a screening station arranged for screening the particulate hemp.

22. The method according to claim 1 wherein the first size range is defined as 25 microns to 500 microns.

23. The system according to claim 11 wherein the first size range is defined as 25 microns to 500 microns.

* * * * *